US009468489B2

(12) United States Patent
Hosier

(10) Patent No.: US 9,468,489 B2
(45) Date of Patent: Oct. 18, 2016

(54) ELECTROSURGICAL SYSTEM

(75) Inventor: John Roland Hosier, Cardiff (GB)

(73) Assignee: GYRUS MEDICAL LIMITED, St. Mellons, Cardiff (GB)

( * ) Notice: Subject to any disclaimer, the term of this patent is extended or adjusted under 35 U.S.C. 154(b) by 951 days.

(21) Appl. No.: 13/252,493

(22) Filed: Oct. 4, 2011

(65) Prior Publication Data
US 2012/0083779 A1 Apr. 5, 2012

(30) Foreign Application Priority Data
Oct. 5, 2010 (GB) .................................. 1016709.6

(51) Int. Cl.
A61B 18/18 (2006.01)
A61B 18/12 (2006.01)
A61B 18/00 (2006.01)

(52) U.S. Cl.
CPC ........ *A61B 18/1233* (2013.01); *A61B 18/1206* (2013.01); *A61B 2018/00196* (2013.01); *A61B 2018/00589* (2013.01); *A61B 2018/00601* (2013.01)

(58) Field of Classification Search
CPC ................ A61B 18/1206; A61B 2018/00702; A61B 2018/00875
USPC ........................................... 606/51, 33, 130
See application file for complete search history.

(56) References Cited

U.S. PATENT DOCUMENTS

| 3,866,602 A * | 2/1975 | Furihata ........................ 600/103 |
|---|---|---|
| 4,114,623 A | 9/1978 | Meinke et al. |
| 4,209,018 A | 6/1980 | Meinke et al. |
| 4,860,745 A | 8/1989 | Farin et al. |
| 5,108,391 A | 4/1992 | Flachenecker et al. |
| 5,312,401 A | 5/1994 | Newton et al. |
| 5,843,019 A * | 12/1998 | Eggers et al. .................. 604/22 |
| 5,976,128 A | 11/1999 | Schilling et al. |
| 6,547,786 B1 | 4/2003 | Goble |
| 2008/0082095 A1* | 4/2008 | Shores et al. ................... 606/34 |
| 2008/0082096 A1* | 4/2008 | Shores et al. ................... 606/34 |

FOREIGN PATENT DOCUMENTS

EP 2 108 325 A1 10/2009

OTHER PUBLICATIONS

GYRUS ACMI ; Maintenance and Repair Manual, G400 Workstation Model 777000; Dec. 18, 2008; Issue: 877111-AB.
GYRUS ACMI; Biomed Service Manual, Electrosurgical Generator G3 RF Workstation; Jul. 25, 2007; Issue: 861084-B.
GYRUS ACMI; Biomed Service Manual, Electrosurgical Generator G400 Workstation Model 777000; Aug. 11, 2009; Part No. 177079-AB.
British Search Report dated Jan. 27, 2011 in British Patent Application No. 1016709.6.
British Search Report dated Jan. 13, 2012 in British Patent Application No. 1117180.8.

* cited by examiner

*Primary Examiner* — Alyssa M Alter
(74) *Attorney, Agent, or Firm* — Oliff PLC

(57) ABSTRACT

A method of controlling an electrosurgical system is described, the system including an electrosurgical generator and an electrosurgical instrument connected to the generator by means of a cable. A radio frequency signal is supplied to the electrosurgical instrument at an operating frequency, and the voltage of the radio frequency signal is monitored at a frequency corresponding to the frequency of a resonant circuit established by the electrosurgical instrument together with the cable. The monitored voltage is capable of indicating the initiation of arcing from the electrosurgical instrument, such that the voltage of the radio frequency signal can be adjusted in response to the monitored voltage at the resonant frequency. The magnitude of the monitored voltage is an indication of the degree of arcing. An electrosurgical system including an arc detector is also disclosed.

21 Claims, 6 Drawing Sheets

ELECTROSURGICAL SYSTEM

FIELD OF THE INVENTION

This invention relates to a method of controlling an electrosurgical system suitable for the treatment of tissue. Such systems are commonly used for the vaporization and/or coagulation of tissue in surgical intervention, most commonly in "keyhole" or minimally invasive surgery, but also in "open" surgery. The invention also includes an electrosurgical system comprising an electrosurgical generator, an electrosurgical instrument and a cable interconnecting the generator and the instrument.

BACKGROUND OF THE INVENTION

There is frequently a requirement to detect the onset of arcing from an electrosurgical instrument, either in order to control the operation of the instrument, or because such arcing is considered undesirable in the circumstances. Examples of arc detection systems are U.S. Pat. No. 4,114,623, U.S. Pat. No. 5,976,128, U.S. Pat. No. 4,209,018, U.S. Pat. No. 4,860,745 and U.S. Pat. No. 5,108,391. Most of the above patents disclose the monitoring of the energy related to the non-zero harmonic frequencies of the operating radio frequency signal in order to detect arcing in fixed frequency monopolar systems. The present invention attempts to provide an improved type of arc detection system, without some of the limitations of such prior art systems.

SUMMARY OF THE INVENTION

Accordingly, in one aspect of the invention, a method of controlling an electrosurgical system is provided, the electrosurgical system including an electrosurgical generator and an electrosurgical instrument connected to the generator by means of a cable, the method comprising the steps of:

(i) supplying a radio frequency signal to the electrosurgical instrument at an operating frequency, (ii) monitoring the voltage of the circuit supplying the radio frequency signal at a frequency corresponding to the frequency of a resonant circuit established by the electrosurgical instrument together with the cable, the monitored voltage being capable of indicating the initiation of arcing from the electrosurgical instrument, and (iii) adjusting the magnitude of the radio frequency voltage in response to the monitored voltage at the resonant frequency.

In the prior art systems discussed above, the radio frequency (RF) energy is supplied via two separate wires, an active one, and one that connects to a 'return pad' placed on the patient's body. These two wires are physically separated by a comparative large unspecified distance, and as a consequence the electrical waveform seen at the generator end of the connection is a representation of that produced by the arcing activity. The systems referred to in the above patents are devised to detect this. These systems also work on a fixed frequency RF system as they need to use filters. In a RF system that is load dependent such that it exhibits a variable frequency, the filters would have to be tracking types and thus very difficult to implement in the analogue domain.

In variable frequency bipolar electrosurgical systems where the fundamental radio frequency is directly proportional to the load impedance (which is mainly resistive), the two wires connecting the electrodes are physically implemented in a cable assembly. They are thus held a constant, relatively small distance apart, and as a consequence of this, the waveform seen at the generator end of the cable when an arc occurs is modified by the characteristics of the cable and no longer is a direct representation of the arc itself as in the systems above. The arc waveform seen at the generator has been modified by the electrical characteristics of the cable assembly. Thus the above systems would be ineffective in detecting the arcs in such cable connected bipolar systems.

While not restricted to use with variable frequency bipolar systems, the present invention is particularly suited to providing an arc detection system for such circumstances. Once an arc has occurred, the medium around the electrodes (typically air or a saline solution) contains ionised particles that easily promote subsequent arcs, and these are of a greater energy because there are more ionised particles to take part. Thus it is common for an arc to be followed by a series of more energetic arcs. In a saline environment the RF is used to form arcing between the two electrodes. This is the desired effect, but arcs to other metal objects in the surgical site can occur and this is undesirable.

In an electrosurgical system the source of the RF energy, the RF generator, is connected to the electrode assembly by a cable. In bipolar systems the current flows through two wires (an active and return); these are physically next to each other in a cable assembly. This can be regarded as a transmission line with characteristic lumped equivalent circuit components (series inductance, L, parallel capacitance, C, series resistance, R). These equivalent circuit elements have a 'natural' frequency at which they resonate or 'ring' if suitably energised. The normal range of frequencies of the applied RF energy and its non-zero harmonics are below the resonant frequency of the cable and do not make it ring. An arc is an energy event that has a very short life time. This time is of an order of magnitude that makes the cable assembly resonate at its natural frequency, but the cable equivalent circuit is heavily damped so that oscillations do not build up, but instead decay very quickly. The mathematical transformation of a short pulse in the time domain into the frequency domain yields a sine series with a high frequency fundamental. When this fundamental is near to the resonant frequency of the cable parasitic equivalent elements, the pulse energy is transferred along the cable and can therefore be detected at the generator end of the system. The duration of the arc is variable and this produces a variation in the fundamental frequency of the resulting voltage on the cable. The 'Q' of the cable elements is low so this aids in the voltage being detectable at the generator end of the system. The voltage present at the generator end of the cable is not that directly produced by the arc, but one modified by the effect of the cable.

In a saline system the desired arcing has a frequency spectrum nearer to that of the energising RF, whereas any unwanted arcs will have frequency components as described above.

By using these high frequency components at the generator end of an electrosurgical system, which are not normally present in the desired RF waveform, the arcing can be detected and controlled more quickly and effectively as compared with typical prior art systems.

Conveniently, the step of adjusting the voltage of the radio frequency signal comprises reducing the magnitude of the voltage to a level insufficient to cause unwanted arcing from the electrosurgical instrument. Preferably, the voltage is temporarily reduced for a preset period of time before being re-established at its original level. In this way, any undesired arcing can be suppressed, but the overall operation of the electrosurgical instrument may continue relatively unaffected. If the arcing occurs again, the voltage will again be reduced, and if this continues, the electrosurgical instrument will need to be cleaned or changed, or otherwise investigated to establish why arcing is continuing to occur. Perhaps the electrosurgical instrument will need to be repositioned, possibly because it is too close to another conductive component or instrument. Sometimes, the arcing is a single event, in which case the voltage is automatically re-established by the electrosurgical generator and the procedure can continue uninterrupted.

The frequency of the monitored voltage is preferably unrelated to the operating frequency of the RF signal. Typically, the operating frequency of the RF signal is below 500 kHz and may be variable, e.g. according to the load presented to the generator, whereas the frequency of the monitored voltage is in the range 10 MHz to 25 MHz. This means that the frequency of the monitored voltage is typically at least 30 times the operating frequency of the RF output signal. This is very different from the prior art systems mentioned above, which detect the voltage levels at a fixed frequency related to non-zero harmonic frequencies of the RF operating signal, which are typically of the order of a few multiples of the RF operating frequency.

The monitored voltage is preferably one occurring at the basic resonant frequency of the resonant circuit established by the electrosurgical instrument together with the cable. This is typically somewhere around 20 MHz: well above the operating frequency of the radio frequency signal and its normally occurring non-zero harmonics. Alternatively, the monitored voltage is one occurring at a harmonic frequency of the resonant circuit established by the electrosurgical instrument together with the cable. This is at an even higher frequency, typically around 40 MHz or even higher. Whether the frequency being monitored is the basic frequency of resonance of the cable or a harmonic thereof, this frequency is well above the operating frequency of the radio frequency signal or the detectable harmonics thereof, which are typically at a frequency of around 2 MHz. Higher harmonics of the RF output signal have a much lower amplitude and, as the number if the harmonic rises, quickly become undetectable for practical purposes.

According to another aspect of the invention, there is provided a method of controlling an electrosurgical system including an electrosurgical generator and an electrosurgical instrument connected to the generator by means of a cable, wherein the method comprises the steps of: (i) supplying radio frequency (RF) energy to the instrument as an RF output signal at a generator operating frequency; (ii) monitoring the voltage of the RF output signal at a frequency at least 30 times the generator operating frequency, the monitoring frequency being a frequency corresponding to that of a ringing signal component produced when arcing occurs at the electrosurgical instrument: and (iii) adjusting the voltage magnitude of RF output signal in response to the voltage at the monitoring frequency.

According to a further aspect of the invention, an electrosurgical system comprises; an electrosurgical generator for generating radio frequency (RF) energy for delivery as an RF output signal at a generator output and at a generator operating frequency; an electrosurgical instrument including at least one treatment electrode; and a cable for connecting the instrument to the generator output to supply the RF output signal to the said electrode; wherein the system further comprises an arc detector having a monitoring input coupled to the cable and the instrument, and a detection output coupled to a signalling input of the generator, the arc detector being arranged to monitor via its monitoring input the supplied RF output signal, to detect in the supplied RF output signal a ringing signal component at a frequency corresponding to the resonant frequency of a resonant circuit established by the instrument together with the cable, and to produce, in response to the detected ringing signal component, a detection signal at the detection output which is fed to the generator signalling input, and wherein the arc detector and the generator are arranged such that the supplied RF output signal is adjusted in response to the detection signal fed to the generator signalling input. In the preferred system, the generator has an RF output stage with a pair of output terminals, and a control stage coupled to the RF output stage for controlling the delivery of RF energy to the output terminals. The preferred instrument is a bipolar instrument having at least two treatment electrodes together forming an electrode assembly, each treatment electrode being connectable to one of the output terminals of the generator output stage via wires in the cable. The arc detector is preferably contained in the generator and has input lines coupled to the generator output terminals to monitor a parameter of the RF signal appearing across the output terminals in particular a ringing signal component occurring at the resonant frequency of the resonant circuit including the cable. The arc detector has a detection output coupled to an input of the generator control stage so that, when the arc detector detects a ringing signal component at a monitoring frequency of the arc detector, the control stage adjusts the RF energy delivered to the generator output terminals to a lower level (which may be zero) so as automatically to quench the arc.

The arc detector of the preferred embodiment of the invention has a tuned input amplifier, a peak detector with a fast-attack/slow-decay characteristic, and a comparator stage receiving a pre-determined reference input and operable to produce a switching output which changes state when the monitored ringing signal component reaches a predetermined threshold at the monitoring frequency. The generator coated stages is arranged to interrupt the RF output signal from the generator in response to the change of state of the comparator output, the original output signal voltage being re-established after a short period.

The invention also includes an electrosurgical system comprising: an electrosurgical generator for generating radiofrequency (RF) energy for delivery as an RF output signal at a generator output and at a generator operating frequency; an electrosurgical instrument including at least one treatment electrode; and a cable for connecting the instrument to the generator output to supply the RF output signal to the said electrode; wherein the system further comprises an arc detector having a monitoring input coupled to the cable and the instrument, and a detection output coupled to a signalling input of the generator, the arc detector being arranged to monitor via its monitoring input the supplied RF output signal, to detect in the supplied RF output signal a ringing signal component at a frequency at least 30 times the generator operating frequency, and to produce, in response to the detected ringing signal component, a detection signal at the detection output for feeding to the generator signalling input, and wherein the arc detector and the generator are arranged such that the supplied RF output signal is adjusted in response to the detection signal fed to the generator signalling input.

The methods of the present invention are suitable for use in an electrosurgical system wherein the electrosurgical instrument is an endoscopic instrument. Typically undesirable arcing can occur between the electrosurgical instrument and other endoscopic accessories and devices, such as resectoscopes, endoscopes or cameras. Such arcing, if left unchecked, disrupts the endoscopic surgical procedure, and can even damage the camera or other device, or the electrosurgical instrument itself. The arc detection method described hereinafter prevents such damage, and allows the procedure to continue if the circumstances causing the arcing have abated. The method of the present invention is also suitable for use in an electrosurgical system wherein the electrosurgical instrument is a multipolar electrosurgical instrument, such as a bipolar instrument, tripolar instrument or an instrument with even more electrodes. In this event, arcing can occur between the electrodes of the electrosurgical instrument. This can be caused by the insulation between the electrodes breaking down, typically because debris such as carbonised tissue has become attached to the instrument creating a conductive track between the electrodes. The present monitoring system detects such arcing quickly and efficiently, allowing the interruption of the electrosurgical signal before excessive damage is caused to the electrosurgical instrument.

The invention will now be further described, by way of example only, with reference to the accompanying drawings.

DETAILED DESCRIPTION OF THE PREFERRED EMBODIMENTS OF THE INVENTION

Figure 1:
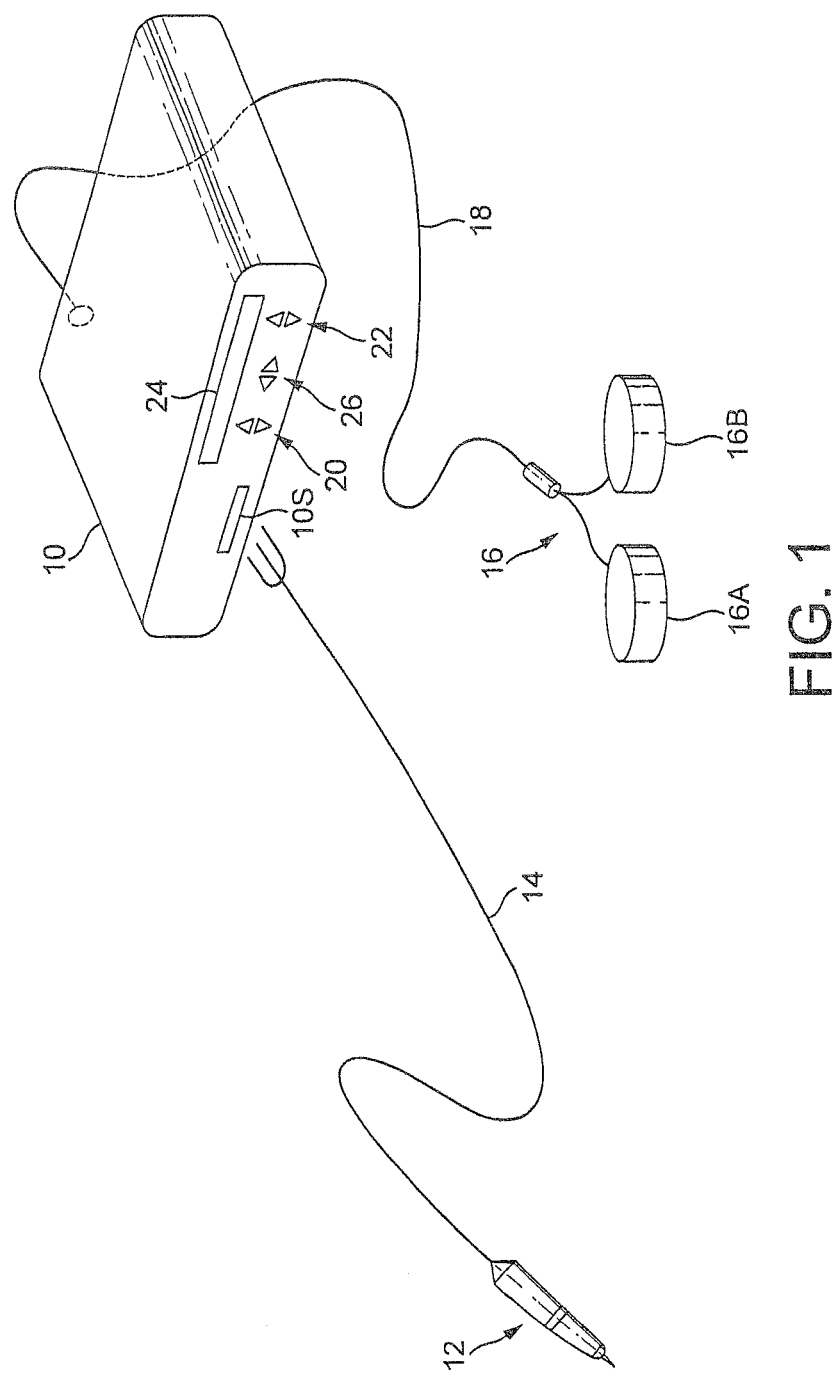
FIG. 1 is a schematic diagram of an electrosurgical system suitable for practicing the method of the present invention.

Referring to FIG. 1, a generator 10 has an output socket 10S providing a radio frequency (RF) output for an instrument 12 via a connection cord 14. Activation of the generator may be performed from the instrument 12 via a connection cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting cutting and coagulation power levels, which are indicated in a display 24. Push buttons 26 are provided as a means for selection between alternative coagulation and cutting waveforms.

Figure 2:
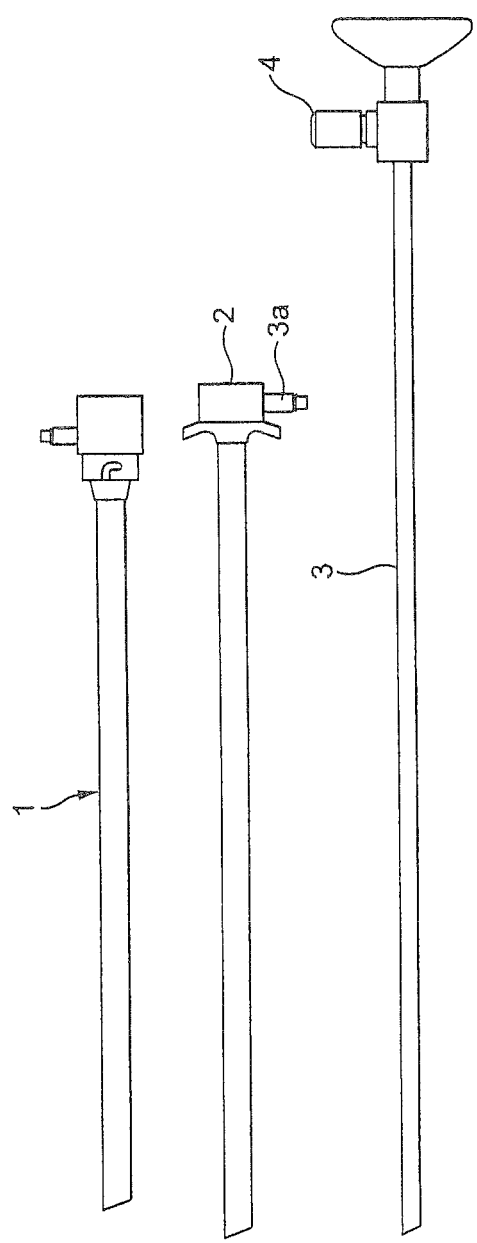
FIG. 2 is a side view of particular components making up an alternative embodiment of instrument which is a part of the system of FIG. 1.
Figure 3:
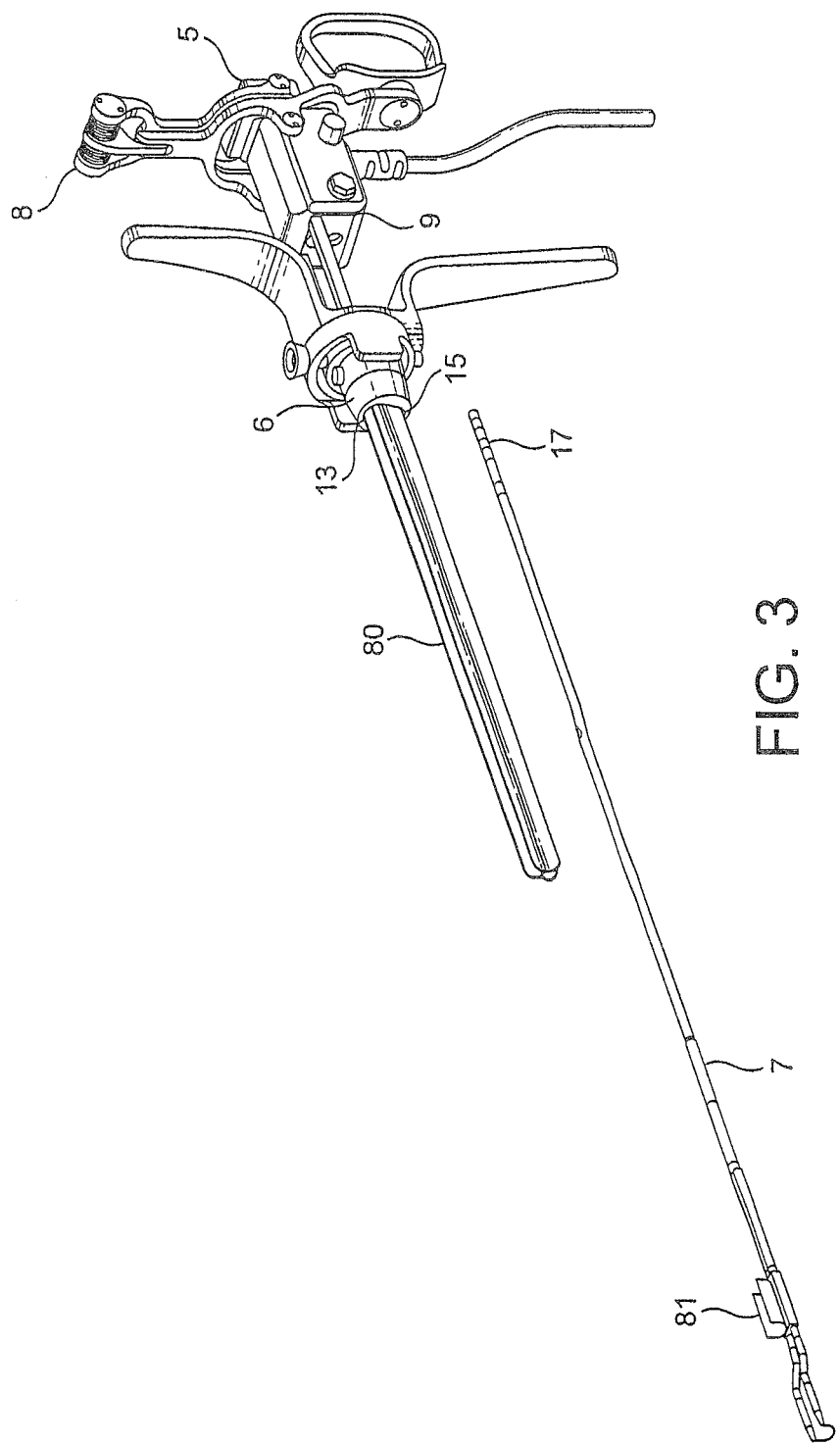
FIG. 3 is a perspective view of other particular components making up the instrument which is a part of the system of FIG. 1.

FIGS. 2 and 3 show an embodiment of the instrument 12 in more detail. As shown in FIGS. 2 and 3, the instrument is in the form of a resectoscope consisting of several main components, an inner sheath 1, an outer sheath 2, a rod lens telescope/light source assembly 3, a working element 11, and a bipolar electrode assembly 7. The sheaths 1 and 2 provide for the supply and aspiration of an operating site with a fluid medium via a connector 3a. The outer sheath 2 locks over the inner sheath 1, forming a watertight seal. Typically, the inner sheath 1 has a diameter of 24 Fr, and the outer sheath 2 has a diameter of 27 Fr. The telescope assembly 3 provides the means of illuminating and viewing the operative site via a light source (not shown) connected thereto by a connector 4. The viewing angle of the telescope is generally at 30° to its axis.

The working element 11 may be either passive or active, that is to say the cutting stroke of the electrode may be as the result of a spring bias or against the force of a spring bias. The telescope assembly 3 is received within the working assembly 11 by means of a telescope connector 5 at its proximal end. The telescope assembly passes through a sealing block 6 having an aperture 13 therein, the inner sheath 1 also being connected to the sealing block. Both of these interfaces are watertight. A support guide 80 is provided on the distal side of the sealing block 6. Two spring-loaded links 8 and an insulation block 9, located between the sealing block 6 and the telescope connector 5, make up the mechanism. The active mechanism is arranged so that the spring-loaded links 8 assist the forward stroke, while, in the passive version the links aid the backward stroke. In general, the range of travel is about 25 mm.

An aperture 13 in the sealing block 6 allows the telescope support assembly 3 to be passed from the proximal to the distal end of the working element 11, within the bore of the inner sheath 1. The aperture 13 is offset, so that the telescope is located in the upper quadrant of the support guide 80 to make room for the electrode assembly 7.

The electrode assembly 7 can be inserted down the support guide 80 from the distal end thereof, and through a second aperture 15 in the sealing block 6. A plug portion 17 is provided at the proximal end of the electrode 7, and this plug portion is received within a socket located within the aperture 15. A telescope clip 81, provided on the electrode 7, ensures radial alignment of the electrode with respect to the working element 11, and this may be enhanced with other features such as a bevelled end face (not shown) which may be present on the plug portion 17. Other features, such as detents or other locking mechanisms (not shown) may be present between the plug portion 17 and the socket located within the aperture 15, in order to ensure longitudinal alignment and complete engagement therebetween.

In use the telescope 3 is used to view the surgical site, and the electrode assembly 7 is used to excise and/or coagulate tissue. However, should the electrode assembly inadvertently come into contact with the telescope 3 (or any other conductive components in the vicinity of the electrode assembly) arcing may occur between the electrode assembly 7 and the telescope 3. A circuit capable of detecting such arcing before significant damage occurs is described hereinafter.

Figure 4:
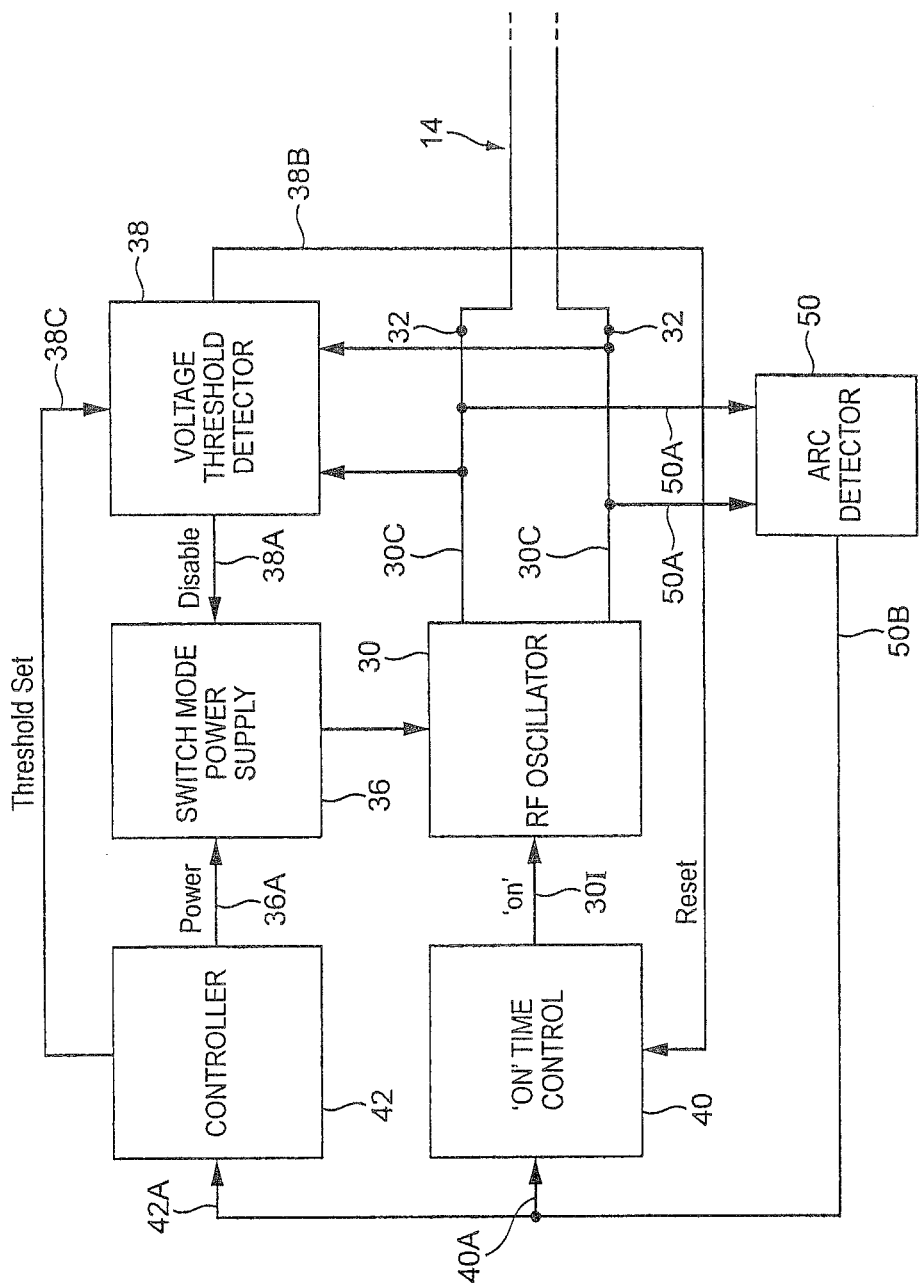
FIG. 4 is a block diagram of an electrosurgical generator forming part of the system of FIG. 1.

Referring to FIG. 4, the generator of the electrosurgical system of FIG. 1 comprises an RF power oscillator 30 having a pair of output lines 30C for coupling via output terminals 32 to a cable 14. At its end remote from the generator output terminals 32, the cable is connected to an electrosurgical instrument 12, as shown in FIG. 1. Power is supplied to the oscillator 30 by a switched mode power supply 36.

In the preferred embodiment, the RF oscillator 30 operates at about 400 kHz, with any frequency from 300 kHz upwards into the HF range being feasible. Coupled across the output lines 30C is a voltage threshold detector 38 having a first output 38A coupled to the switched mode power supply 36 and a second output 38B coupled to an "on" time control circuit 40. The generator also contains a microprocessor controller 42 coupled to operator controls and a display (shown in FIG. 1) and, in addition, to a control input 36A of the power supply 36 for adjusting the generator output power by supply voltage variation and to a threshold-set input 38C of the voltage threshold detector 38 for setting peak RF output voltage limits. The "on" time control circuit 40 and the controller 42 together form a control stage of the generator.

In operation, the controller 42 causes power to be applied to the switched mode power supply 36 when electrosurgical power is demanded by the surgeon operating an activation switch arrangement which may be provided in the handheld instrument 12 or foot switches 16A, 16B (see FIG. 1). A constant output voltage threshold is set independently of the supply voltage via input 38C according to control settings on the front panel of the generator (see FIG. 1). Different threshold voltages are set according to whether coagulation or cutting is required.

The "on" time control circuit 40 is normally "on" so that the power switching device which forms the oscillating element of the RF oscillator 30 is switched on for a maximum conduction period during each oscillation cycle. This status is maintained via the control input 60I of the oscillator 60, which input is coupled to the "on" time control circuit 40. The "on" time control circuit 40 has the effect of virtually instantaneously reducing the "on" time of the RF oscillator switching device when the voltage threshold set in the voltage threshold detector 38 is reached, as signalled by a corresponding signal on the second output 38B of the threshold detector 38. The operation of the generator in this way is described in detail in EP 0754437, the disclosure of which is hereby incorporated by way of reference.

Also coupled across the output lines 30C is an arc detector circuit 50 having monitoring input lines 50A and a detector output 50B, the latter being coupled to signalling inputs 40A of the "on" time control circuit 40 and 42A of the controller 42. Since the cable 14 and the instrument 12 (FIG. 1) are connected to the generator output terminals 32, the monitoring input lines 50A of the arc detector 50 are connected across the combination of the cable 14 and the electrosurgical instrument. This cable and instrument combination has a natural resonance and the arc detector is configured to sense a ringing signal voltage across the generator output terminals 32 at the frequency of this natural resonance.

Figure 5:
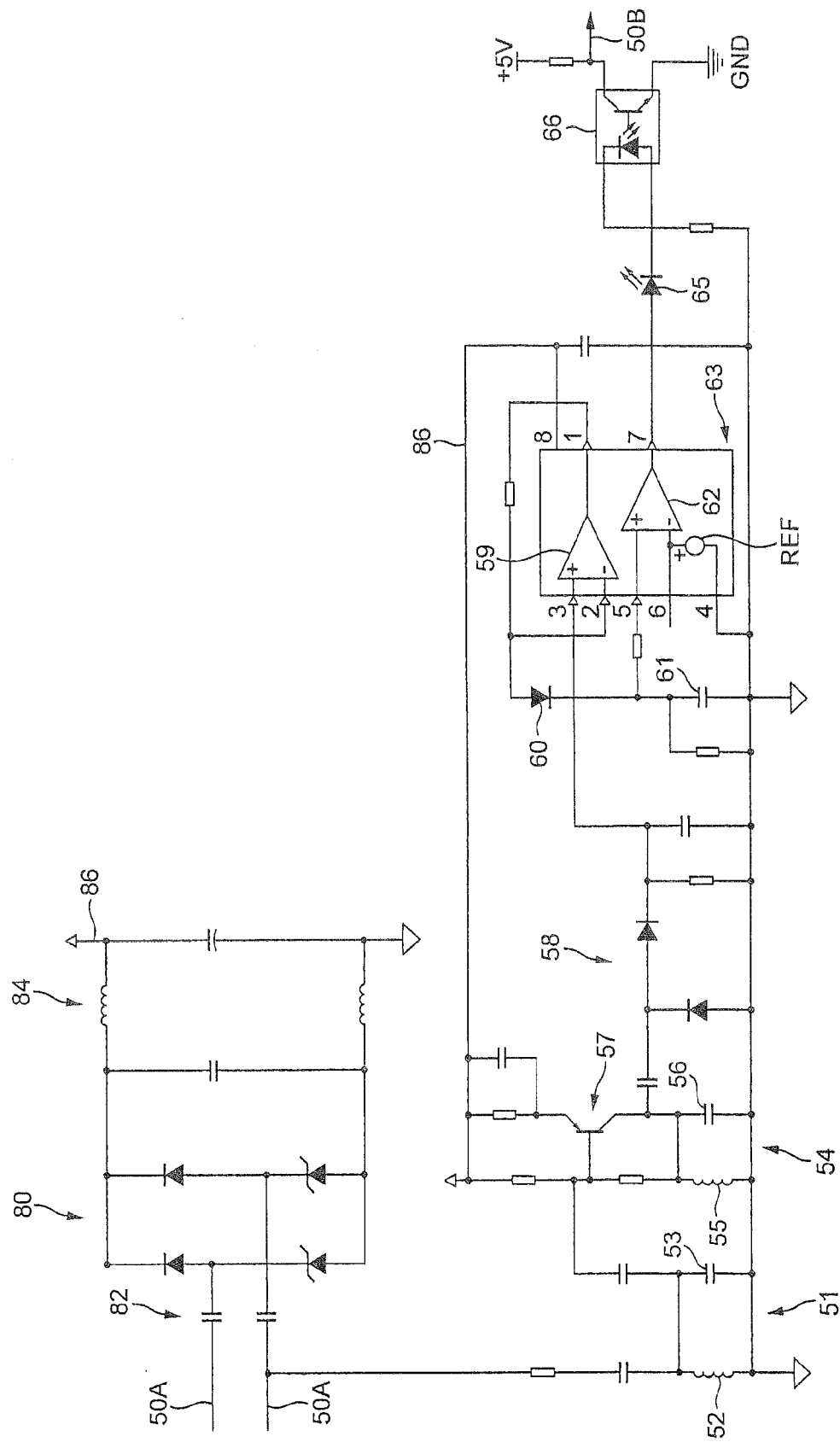
FIG. 5 is a circuit diagram of an arcing detection circuit suitable for practising the method of the present invention.

Referring to FIG. 5, the arc detector 50 has, connected to its input lines 50A, a first tuned filter 51 consisting of inductor 52 and capacitor 53, the filter being tuned to a frequency of around 16 MHz. The output from the tuned filter 51 is input to a second tuned filter 54, consisting of an inductor 55 and a capacitor 56, via a buffer amplifier 57. The tuned filter 54 has a high Q-factor so as to select voltages at a specified frequency only, the specified frequency being the resonant frequency of the instrument 12 together with its cable 14. The output from the second tuned filter 54 is input to a diode peak detector 58. This forms a stable DC voltage that is directly proportional to the peak arc voltage activity. This DC voltage is buffered by operational amplifier 59. Diode 60 is used with a capacitor 61 to form a voltage for a comparator 62 that has a defined fast attack and slow decay characteristic. The output of the buffer 59 is taken to a comparator circuit 63 including the comparator 62, which is designed to give a positive output when the amplitude of the voltage at the resonant frequency exceeds a threshold level set by a stable and accurate band gap reference. In this example the comparator circuit 63 is an integrated circuit type MAX951ESA+ available from Maxim Integrated Products. When this occurs a signal is output at line 50B via an indicator LED 65 and an optoisolator 66 to signal to the generator 10 via the input 42A to the controller 42, as described above with reference to FIG. 4. The controller 42 reduces the operating RF voltage for a preset period of time. One feature of the arc detector circuit 50, as shown in FIG. 5, is that it is powered from the RF output lines of the generator. A rectifier bridge 80 receives RF energy via a pair of small value capacitors 82. The resulting rectified RF signal is smoothed by a smoothing circuit 84 to yield a 5 volt supply voltage on supply rail 86. The voltage of the supply rail is set at 5 volts by two zener diodes in the bridge 80.

Referring to FIGS. 4 and 5 together, the connection of the arc detector output 50B to the "on" time control circuit 40 provides a hardware-based control function which can respond very rapidly to arcing at the electrosurgical instrument working end. As described in EP0754437, the "on" time control circuit 40 is arranged to vary the conduction time of an RF power device in the RF oscillator 30. This power device is typically an IGBT (insulated gate bipolar transistor) operating effectively in a switching mode to pump an output tank circuit at the generator operating frequency. The "on" time control circuit 40 has a driver for the gate of the IGBT and the driver is fed from a variable pulse width source operating at the generator operating frequency and synchronized to the RF output from the IGBT. When the output device 66 of the arc detector changes state as a result of ringing on the arc detector input lines 50A, the resulting signal transmitted to the "on" time control circuit 40 via its signalling input 40A causes the pulse width of the variable pulse width source to be reduced to a minimum, typically half of the previous value, with the result that the RF power device in the RF oscillator 30 operates at a low level with a very short "on" time in each RF cycle. The effect of this is to reduce the substantially sinusoidal RF output signal from the output terminals 32 of the generator to half its previous voltage magnitude. Using a minimum value of gate drive also maintains the phase relationship of the drive signal to the RF tank voltage for when the normal operation is resumed, i.e. when the arcing has ceased.

The output 50B of the arc detector 50 is also connected to the controller 42 at its signalling input 42A to signal the presence of arcing to the software-controlled part of the control stage.

When arcing starts to occur between the electrode assembly 7 and the telescope 3, a voltage signal is generated at the resonant frequency of the combination of the instrument 12 and cable 14 (the frequency being determined mainly by the capacitance of the cable 14). The arc detector detects the increased voltage at this frequency, and the control stage of the generator instructs the generator to reduce the magnitude of the operating radio frequency voltage to the instrument 12, this process including the reduction of the RF output signal instantly via a direct circuit link to the driver for the RF power device in the generator RF output stage. In this case this is achieved by reducing the "on" time of the switching RF power device, i.e. by pulse-width control as described above. This causes the arcing to stop before any significant damage is caused. After a predetermined period of time (typically 0.5 seconds), set, in this embodiment, by the arc detector 50, the magnitude of the operating voltage is re-established in an attempt to continue the procedure. If the arcing re-occurs, the arc detector and the control stage again operate to reduce the voltage. Typically, if the operating voltage is re-established more than 5 times and arcing starts to occur each time, the generator controller 42 causes the generator to switch to standby and display a message warning that the system should be checked before continuing.

Figure 6:
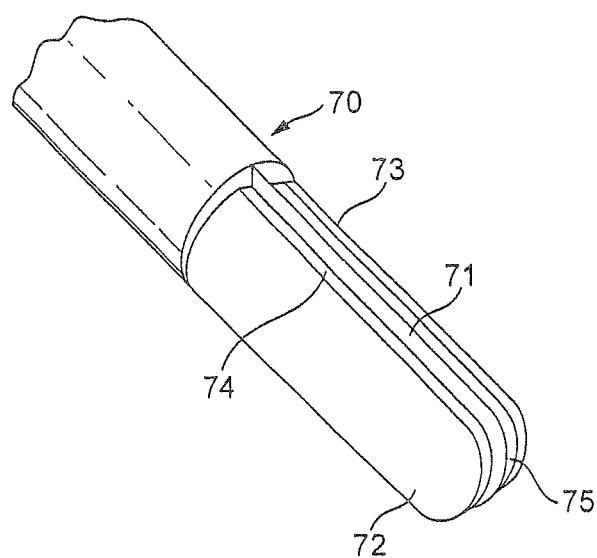
FIG. 6 is a schematic diagram of an alternative instrument which is part of the system of FIG. 1.

The telescope is not the only component susceptible to arcing from the electrode assembly 7. FIG. 6 shows a bipolar electrosurgical instrument 70 including a series of electrodes in a sandwich formation. Cutting electrode 71 is contained between outer electrodes 72 and 73. Insulating layer 74 is present between electrodes 71 and 72, while insulating layer 75 is present between electrodes 71 and 73. The operation of the instrument of FIG. 6 is described in more detail in U.S. Pat. No. 7,211,084.

During use of the instrument of FIG. 6, it is possible that eschar or other tissue debris can build up on the instrument, causing a conductive track to form between electrodes 71 and 72, or electrodes 71 and 73. This causes arcing to occur, a condition known as "flare-out". The arc detector of FIG. 5 detects this arcing as previously described, and reduces the operating voltage to allow the flare-out to subside. Many times this will be sufficient for the eschar or other debris to be dislodged, such that the instrument will operate normally when the operating voltage is re-established. However, if the conductive track is still present on the instrument, arcing will re-occur such that the arc detector will operate successively until the generator switches to standby and displays a message suggesting that the instrument be cleaned or replaced.

Since the are detector of FIG. 5 detects voltage changes at a relatively high frequency, it allows a rapid response to any arcing being initiated. This allows action to be taken to mitigate the arcing before any damage is done, either to the electrosurgical instrument or to any associated surgical accessories and devices.

What is claimed is:

1. A method of controlling an electrosurgical system including an electrosurgical generator and an electrosurgical instrument connected to the generator by means of a cable, the method comprising the steps of
   (i) supplying a radio frequency signal to the electrosurgical instrument at an operating frequency,
   (ii) monitoring a voltage of the radio frequency signal at a monitoring frequency corresponding to a frequency of a resonant circuit established by the electrosurgical instrument together with the cable, the monitored voltage being capable of indicating an initiation of arcing from the electrosurgical instrument, and the monitoring frequency being in the range 10 MHz to 25 MHz and different from and not overlapping with the operating frequency of the radio frequency signal or any of its non-zero harmonics, and
   (iii) adjusting the magnitude of the radio frequency voltage at the operating frequency in response to the monitored voltage at the monitoring frequency.

2. A method of controlling an electrosurgical system according to claim 1, wherein the step of adjusting the voltage of the radio frequency signal comprises reducing the magnitude of the voltage to a level insufficient to cause arcing from the electrosurgical instrument.

3. A method of controlling an electrosurgical system according to claim 2, wherein the voltage is temporarily reduced for a preset period of time before being re-established at its original level.

4. A method of controlling an electrosurgical system according to claim 1, wherein the frequency of the monitored voltage is at least 30 times the operating frequency of the radio frequency signal.

5. A method of controlling an electrosurgical system according to claim 1, wherein the monitored voltage is the basic resonant frequency of the resonant circuit established by the electrosurgical instrument together with the cable.

6. A method of controlling an electrosurgical system according to claim 1, wherein the monitored voltage is a harmonic frequency of the resonant circuit established by the electrosurgical instrument together with the cable.

7. A method of controlling an electrosurgical system according to claim 1, wherein the electrosurgical instrument is an endoscopic instrument.

8. A method of controlling an electrosurgical system according to claim 7, wherein the arcing from the electrosurgical instrument is between the electrosurgical instrument and another endoscopic device.

9. A method of controlling an electrosurgical system according to claim 8, wherein the other endoscopic device is an endoscope.

10. A method of controlling an electrosurgical system according to claim 8, wherein the other endoscopic device is an endoscopic camera.

11. A method of controlling an electrosurgical system according to claim 1, wherein the electrosurgical instrument is a multipolar electrosurgical instrument.

12. A method of controlling an electrosurgical system according to claim 11, wherein the electrosurgical instrument is a bipolar electrosurgical instrument.

13. A method of controlling an electrosurgical system according to claim 11, wherein the arcing from the electrosurgical instrument is between the electrodes of the electrosurgical instrument.

14. A method of controlling an electrosurgical system including an electrosurgical generator and an electrosurgical instrument connected to the electrosurgical generator by means of a cable, wherein the method comprises the steps of:
   (i) supplying radio frequency (RF) energy to the electrosurgical instrument as an RF output signal at a generator operating frequency;
   (ii) monitoring a voltage of the RF output signal at a monitoring frequency at least 30 times the electrosurgical generator operating frequency, the monitoring frequency being a frequency corresponding to that of a ringing signal component produced when arcing occurs at the electrosurgical instrument and different from and not overlapping with the operating frequency of the radio frequency signal or any of its non-zero harmonics: and
   (iii) adjusting a magnitude of the voltage of the RF output signal at the operating frequency in response to the voltage at the monitoring frequency.

15. An electrosurgical system comprising;
   an electrosurgical generator for generating radio frequency (RF) energy for delivery as an RF output signal at a generator output and at a generator operating frequency;
   an electrosurgical instrument including at least one treatment electrode; and
   a cable for connecting the instrument to the generator output to supply the RF output signal to the said electrode;
   wherein the electrosurgical system further comprises an arc detector having a monitoring input coupled to the cable and the electrosurgical instrument, and a detection output coupled to a signalling input of the electrosurgical generator, the arc detector being arranged to monitor via its monitoring input the supplied RF output signal, to detect in the supplied RF output signal a ringing signal component at a frequency corresponding to a resonant frequency of a resonant circuit established by the electrosurgical instrument together with the cable, the frequency of the monitored voltage being in a range 10 MHz to 25 MHz and different from and not overlapping with the operating frequency of the radio frequency signal or any of its non-zero harmonics, and to produce, in response to the detected ringing signal component a detection signal at the detection output for feeding to the generator signalling input, and wherein the arc detector and the electrosurgical generator are arranged such that the supplied RF output signal is adjusted in response to the detection signal fed to the generator signalling input.

16. A system according to claim 15, wherein the generator is arranged such that, in response to the said detection signal, the voltage of the supplied RF output signal is reduced to a level insufficient to cause arcing from the electrosurgical instrument.

17. A system according to claim 16, wherein the generator is arranged such that the voltage of the supplied RF output signal is temporarily reduced for a preset period of time and then re-established at its original level.

18. A system according to claim 15, wherein the generator operating frequency is below 500 kHz.

19. A system according to claim 15, wherein the frequency at which the arc detector is operable to detect a ringing signal component is at least 30 times the generator operating frequency.

20. A system according to claim 15, wherein the frequency at which the detector is operable to detect a ringing signal component is the fundamental resonant frequency of the said resonant circuit.

21. An electrosurgical system comprising;
an electrosurgical generator for generating radiofrequency (RF) energy for delivery as an RF output signal at a generator output and at a generator operating frequency;
an electrosurgical instrument including at least one treatment electrode; and
a cable for connecting the electrosurgical instrument to the generator output to supply the RF output signal to the at least one treatment electrode;
wherein the electrosurgical system further comprises:
an arc detector having a monitoring input coupled to the cable and the electrosurgical instrument, and
a detection output coupled to a signalling input of the generator, the arc detector being arranged to monitor via its monitoring input the supplied RF output signal, to detect in the supplied RF output signal a ringing signal component at a frequency at least 30 times the generator operating frequency and different from and not overlapping with the operating frequency of the radio frequency signal or any of its non-zero harmonics, and to produce, in response to the detected ringing signal component, a detection signal at the detection output for feeding to the generator signalling input, and wherein the arc detector and the electrosurgical generator are arranged such that to the supplied RF output signal is adjusted in response to the detection signal fed to the generator signalling input.

* * * * *